(12) United States Patent
Makihara

(10) Patent No.: US 6,383,203 B1
(45) Date of Patent: May 7, 2002

(54) SURGICAL APPARATUS FOR A VITREOUS

(75) Inventor: Kiyoshi Makihara, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 42 days.

(21) Appl. No.: 09/669,727

(22) Filed: Sep. 26, 2000

(30) Foreign Application Priority Data

Sep. 27, 1999 (JP) .......................................... 11-271704

(51) Int. Cl.[7] .............................................. A61B 17/32
(52) U.S. Cl. ........................................ 606/171; 604/22
(58) Field of Search ................................ 606/171, 170, 606/167, 166, 169; 604/22

(56) References Cited

U.S. PATENT DOCUMENTS

| | | | |
|---|---|---|---|
| 4,210,146 A | * | 7/1980 | Banko .......................... 606/171 |
| 4,577,629 A | | 3/1986 | Martinez |
| 4,753,234 A | | 6/1988 | Martinez |
| 4,909,249 A | | 3/1990 | Akkas et al. |
| 5,047,008 A | | 9/1991 | de Juan, Jr. et al. |
| 5,226,910 A | * | 7/1993 | Kajiyama et al. .............. 604/22 |
| 5,275,607 A | | 1/1994 | Lo et al. |
| 5,423,844 A | | 6/1995 | Miller |
| 5,562,691 A | | 10/1996 | Tano et al. |
| 5,873,885 A | | 2/1999 | Weidenbenner |
| 5,916,231 A | | 6/1999 | Bays |
| 6,004,284 A | | 12/1999 | Sussman et al. |

* cited by examiner

Primary Examiner—Kevin Truong
(74) Attorney, Agent, or Firm—Finnegan, Henderson, Farabow, Garrett & Dunner LLP

(57) ABSTRACT

A surgical apparatus for removing a vitreous in an eyeball, comprises a cylinder, a piston disposed in the cylinder so as to be capable of moving, a moving device for reciprocating the piston in the cylinder, and a vitreous cutter. The vitreous cutter comprises a first gas chamber which connects with a second has chamber in the cylinder via a tube, an outer tubular blade having a hole, an inner tubular blade, a moving body which is capable of moving in a longitudinal axial direction of the outer tubular blade with holding the inner tubular blade, and an energisation device which causes the moving body to perform a backward movement toward the opposite side of the hole relative to the outer tubular blade. Where the inner tubular blade and the moving body are caused to perform a forward movement toward the hole relative to the outer tubular blade by a pressure rise in the first gas chamber, the pressure rise being caused by the forward movement of the piston, and to perform the backward movement relative to the outer tubular blade, which is accelerated by a negative pressure by a pressure fall in a second gas chamber connected to the first gas chamber via the tube, the pressure fall being caused by the backward movement of the piston.

8 Claims, 3 Drawing Sheets

SURGICAL APPARATUS FOR A VITREOUS

BACKGROUND OF THE INVENTION

1. Field of the Invention

The present invention relates to a surgical apparatus for a vitreous, and more particularly, to the surgical apparatus which is utilized for removing tissue of a vitreous in an eyeball.

2. Description of Related Art

A vitreous cutter is a handpiece, which is utilized for operating upon a vitreous. The vitreous cutter sucks intraocular tissue through a suction hole, provided on an end of an outer tubular blade, thereby introducing the intraocular tissue therein. With its state, the vitreous cutter removes the tissue by moving an inner tubular blade (a resection blade). Moving methods for an inner tubular blade are the following: a rotary method which causes an inner tubular blade to revolve in one direction; an oscillation method which causes an inner tubular blade to turn clockwise or counterclockwise; a guillotine method which causes an inner tubular blade to reciprocate forwards and backwards (along an axial direction (longitudinal direction) of an outer tubular blade), and the like.

Further, driving methods for moving the inner tubular blade are the following: an electric method which produces an electric power with an electric motor or an electromagnet, provided in a handpiece, to cause an inner tubular blade to move; a pneumatics method which charges with and discharges a compressed-air (gas) intermittently to cause an inner tubular blade to move, and the like. Among these driving methods, at the present time, a pneumatics method is the main current because a handpiece can be lightened and it is disposable.

Herein, a conventional vitreous cutter of a pneumatics type will be described with referring to FIG. 4 (the description is made with respect to a guillotine method). A gas chamber 42 of a vitreous cutter 40 is charged with compressed-air (gas) from a compression pump 41 by a solenoid valve 46. Thereby, a pressure in the gas chamber 42 rises up, its applied pressure pushes and forces a holder 43 to move to a feed (forward) direction (a left direction in FIG. 4). As a result, the inner tubular blade 44 fixed to the holder 43 moves forwards along an outer tubular blade 45 and removes a vitreous body V which is being sucked through a suction hole 45a. After resection (removal), by making the gas chamber 42 communicate with the outside air (atmosphere) with the solenoid valve 46, the air contained in the gas chamber 42 is discharged into outside and the pressure falls down. A spring 47, therefore, forces the inner tubular blade 44 to turn back (backwards) (a right direction in FIG. 4). Reference numeral 48 denotes a muffler fixed to an exhaust hole of the solenoid valve 46 to reduce exhaust noise.

For the purpose of accurate resection of tissue, recently, the following has been required: to reduce an amount of resection during one stroke of the inner tubular blade, but to increase a number of reciprocating motion (a number of stroke) per unit time. Accordingly, it has been important that acceleration of a moving speed of the inner tubular blade.

In the case of a vitreous cutter, however, a return speed of a pneumatics type depends on a spring force, thus there is upper limit in acceleration. To make a spring robust enables an inner tubular blade to accelerate a return speed; but it needs a strong power in order to force the inner tubular blade forwards toward the suction hole. Disadvantageously, a large compression pump (compressor) should be used. Additionally, it is difficult to make an inside spring robust, for the purpose of accelerating an existing (conventional) vitreous cutter of a pneumatics type.

SUMMARY OF THE INVENTION

The present invention has been made in view of the above circumstances and has an object to overcome the above problems and to provide a surgical apparatus for a vitreous, which enables a resection cutter to speed up, and enables the operators to perform the accurate and efficient surgical operation, without making the apparatus large.

To achieve the object and in accordance with the purpose of the present invention, as embodied and broadly described herein, a surgical apparatus for removing a vitreous in an eyeball, comprises a cylinder, a piston disposed in the cylinder so as to be capable of moving, a moving device for reciprocating the piston in the cylinder, and a vitreous cutter. The vitreous cutter comprises a first gas chamber which connects with a second gas chamber in the cylinder via a tube, an outer tubular blade having a hole, an inner tubular blade, a moving body which is capable of moving in a longitudinal axial direction of the outer tubular blade with holding the inner tubular blade, and an energisation device which causes the moving body to perform a backward movement toward the opposite side of the hole relative to the outer tubular blade. The inner tubular blade and the moving body are caused to perform a forward movement toward the hole relative to the outer tubular blade by a pressure rise in the first gas chamber, the pressure rise being caused by the forward movement of the piston, and to perform the backward movement relative to the outer tubular blade, which is accelerated by a negative pressure by a pressure fall in the second gas chamber connected to the first gas chamber via the tube, the pressure fall being caused by the backward movement of the piston.

According to the present invention, a surgical apparatus for a vitreous enables a resection cutter to speed up without making an apparatus large, thus enabling the operators to perform a surgical operation accurately and efficiently. Further the aspect of the present invention may also be applied to the conventional vitreous cutter.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
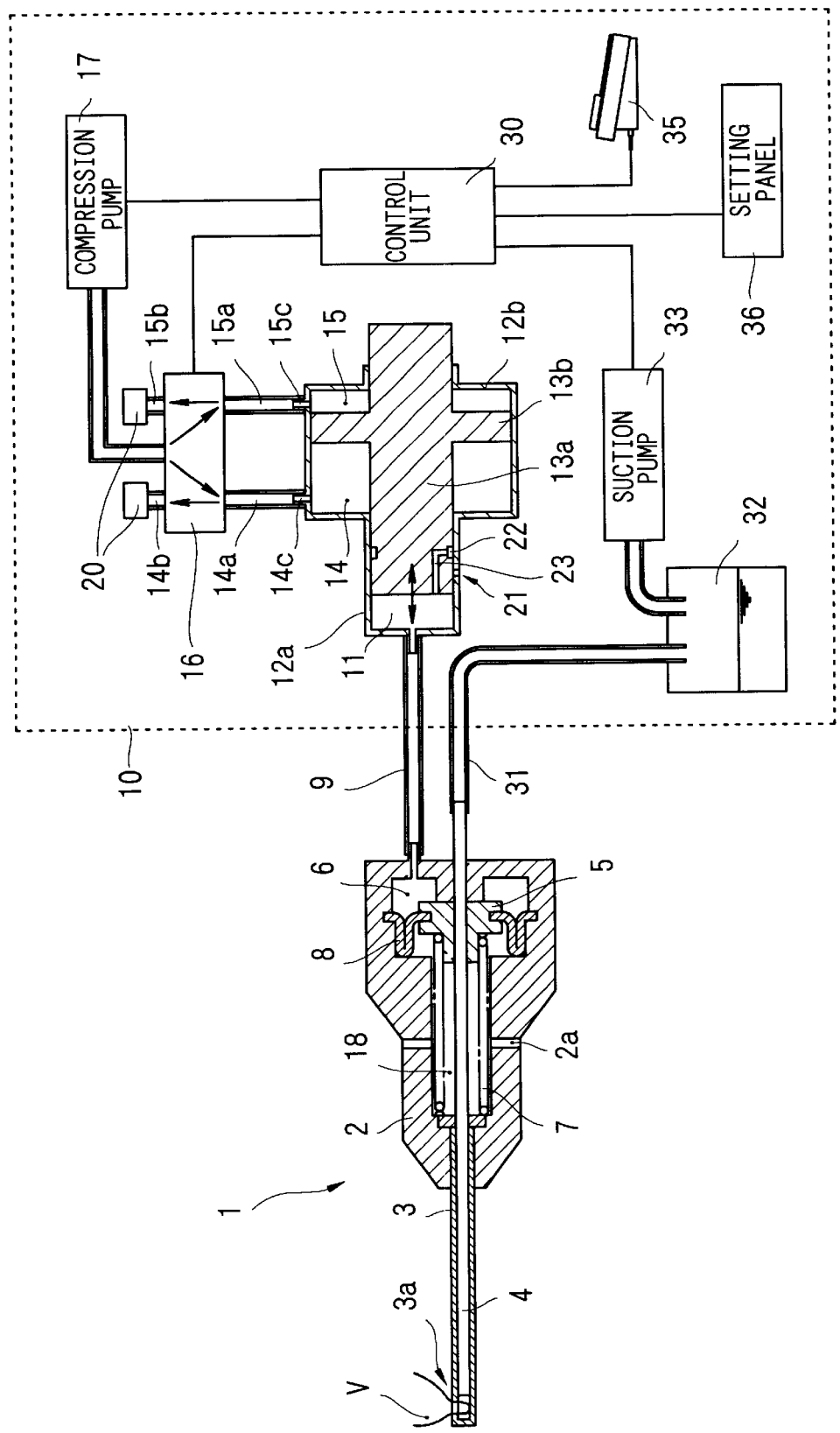
FIG. 1 is a view showing a schematic construction of a surgical apparatus for a vitreous of the preferred embodiment of the present invention.

A detailed description of one preferred embodiment of the present invention will now be given referring to the accompanying drawings. FIG. 1 is a view showing a schematic construction of a surgical apparatus for a vitreous of the preferred embodiment of the present invention.

A vitreous cutter 1 is a handpiece, in which an outer tubular blade 3, provided with a suction hole 3a at its end, is fixed to a housing 2. In the outer tubular blade 3, there is provided an inner tubular blade 4, which is capable of moving in an axial direction (longitudinal direction) of the outer tubular blade 3, with a state fixed to a holder 5. The holder 5 is mounted to the housing 2 with a diaphragm 8 so that the holder can move. A compartment 18 and a gas chamber 6 are composed of the housing 2, the holder 5 and the diaphragm 8.

In the compartment 18, there is provided a spring 7 which forces the holder 5 toward the gas chamber 6 (a right direction in FIG. 1) (a force of the spring 7 acts on the holder 5 backwards (to turn back) (a right direction in FIG. 1)). Further, a hole 2a which connects with the compartment 18 is formed on the housing 2. Even if the movement of the holder 5 induces the volume of the compartment 18 to change, then the air entering or escaping from the hole 2a enables a pressure in the compartment 18 to remain at a constant (an atmospheric pressure). Accordingly, it may be achieved that no unnecessary force act on the holder 5. A conventional cutter can be employed for the cutter 1.

The gas chamber 6 is connected to a gas chamber 11 of a main assembly 10 via a tube 9. The gas chamber 11 is composed of a first cylinder 12a and a first piston 13a. The first cylinder 12a and a second cylinder 12b in one united body incorporates the first piston 13a and a second piston 13b in one united body, to form separate chambers 14 and 15. The separate chambers 14 and 15 are respectively connected to a passage switch 16 via passages 14a and 15a.

Driven by a control unit 30, the passage switch 16, composed of a solenoid valve, enables respective passages 14a and 15a to connect mutually with a compression pump 17. When the passage 15a is connected to the pump 17 then the passage 14a is connected to the exhaust hole 14b open into the outside air, when the passage 14a is connected to the pump 17 then the passage 15a is connected to the exhaust hole 15b. Each exhaust hole 14b and 15b is provided with a muffler 20 to reduce exhaust noise.

Figure 4:
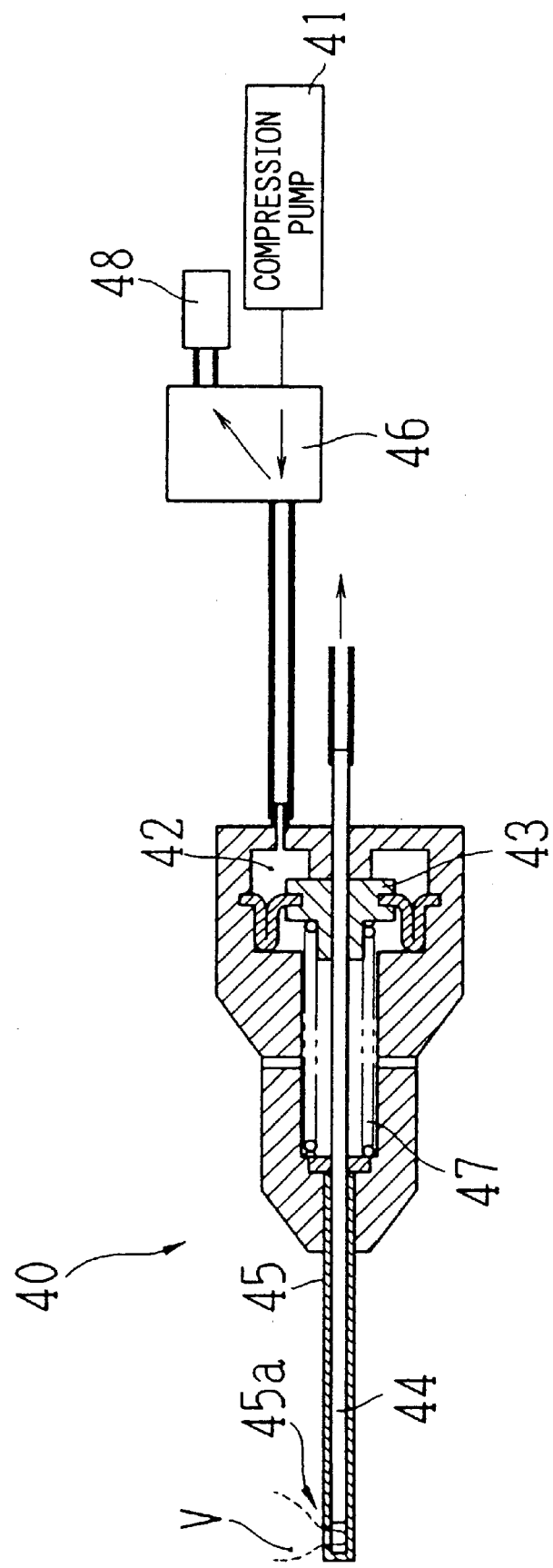
FIG. 4 is a view showing a schematic construction of an important part of a conventional vitreous cutter of a pneumatics type.

To mount the muffler 20 in such location is advantageous because of the following reason. In case of the conventional device as shown in FIG. 4, a muffler 48 was mounted to a solenoid valve 46 directly linked to a cutter 40. This induced a large rise in an exhaust resistance of the air (gas), discharged from the cutter 40. As a result, an inner tubular blade 44 tended to be prevented from returning back. On the contrary, the apparatus of the present invention is provided with the muffler 20 in such a manner as descried above. An exhaust resistance of the air, discharged from the cutter 1, becomes lower than that of the conventional apparatus.

On a side wall of the first cylinder 12a, a cylinder hole 21 open into the outside air is formed. The cylinder hole 21 is formed at such position that is a back side than a bottom dead center on a front end-face of the piston 13a. While, on the middle of a side face of the piston 13a, there is provided a notch 22 composed of a ring gap, from which a connection hole 23 is extended and connects with the gas chamber 11. When the notch 22 agrees with the cylinder hole 21 during a reciprocating motion of the piston 13a, then the gas chamber 11 is brought to be open into the outside air.

The inner tubular blade 4 is connected, via the tube 31, to a drainage chamber 32 to which a suction pump 33 is connected. If a suction pressure is applied to the inside of the inner tubular blade 4 by the pump 33, then a removed vitreous V is sucked from the suction hole 3a and drawn to the drainage chamber 32 via the inner tubular blade 4 and the tube 31.

The control unit 30 drives and controls the passage switch 16, the pump 17, the pump 33 and the like, based on a trigger signal generated by a foot switch 35 and the defined values by using a setting panel 36.

Operations of the apparatus having above described configuration will be given hereinafter.

An operator inserts the outer tubular blade 3 of the cutter 1 into a patient's eye, and arranges the cutter 1 (the outer tubular blade 3) so that the suction hole 3a may agree with a diseased part, such as an opaque part. After that, the operator steps on the foot switch 35, the control unit 30 starts the pumps 17 and 33 running and it further drives the cutter 1 under the given movement speed and suction pressure, defined in advance with the panel 36.

The passage switch 16 switches the passages 14a and 15a to connect with the pump 17, and this enables the inner tubular blade 4 to perform a reciprocating motion. When the pump 17 is connected to the passage 15a, then the separate chamber 15 is charged with the air (gas), compressed by the pump 17. The compressed air, with which the separate chamber 15 is charged, pushes the piston 13b (and the piston 13a in a united body) and starts them performing a forward movement toward the separate chamber 14 (a left direction in FIG. 1). At this time, the separate chamber 14 is open into the outside air, via the passage switch 16, the exhaust hole 14b and the muffler 20. The air from the separate chamber 14, therefore, is discharged into the outside air, thus allowing the pistons 13a and 13b to perform a forward movement smoothly.

When the pistons 13a and 13b starts a forward movement toward the separate chamber 14, then the gas chamber 6 is charged with the air from the gas chamber 11 via the tube 9, with the air being compressed. The compressed and charged air fills up the gas chamber 6 and pushes the holder 5 forwards, thereby causing it to perform a forward movement toward the compartment 18 against a force of the spring 7 (a left direction in FIG. 1). Following the forward movement of the holder 5, the inner tubular blade 4 performs a forward movement along the outer tubular blade 3 and removes the vitreous V, being sucked from the suction hole 3a. The removed vitreous V is discharged into the drainage chamber 32 via the inner tubular blade 4 and the tube 31.

When the pistons 13a and 13b perform a forward movement, then the control unit 30 drives the passage switch 16 to change-over the connection as following: the pump 17 is connected to the passage 14a; and the passage 15a is connected to the exhaust hole 15b. The separate chamber 14 is charged with the air compressed by the pump 17. On the contrary, air from the separate chamber 15 is discharged into the outside air, via the passage switch 16, the exhaust hole 15b, and the muffler 20. This causes the pistons 13a and 13b to start performing a backward movement (a right direction in FIG. 1).

Starting a backward movement of the piston 13a causes the gas chamber 11 to expand, thus causing a pressure in the gas chamber 11 to suddenly fall. When the notch 22 agrees with the cylinder hole 21 during a backward movement of the piston 13a, then a pressure in the gas chamber 11 becomes approximately at an atmospheric pressure through the cylinder hole 21, the notch 22, and the connection hole 23. This mechanism compensates for an air leakage from a connection coupling, such as the tube 9, and a pressure change by a temperature change in the gas chamber As the notch 22 passes through the cylinder hole 21, the piston 13a performs a backward movement further. Accordingly, the notch 22 is disconnected from the cylinder hole 21, thus the gas chamber 11 becomes closed. Therefore, a pressure in the gas chamber 11 falls down to a negative pressure lower than an atmospheric pressure. This pressure fall causes the air from the gas chamber 6 to be suddenly discharged into the gas chamber 11 via the tube 9, this also induces a pressure fall in the gas chamber 6. This produces an attraction force which impels the holder 5 to perform a backward movement. If the attraction force is added to a force of the spring 7, then a speed of a backward movement of the holder 5 is accelerated, thus achieving acceleration of a resection speed. Further, a driving pressure for the cutter 1 can be a high pressure, by making a movement speed of the piston 13a (13b) to rise.

Such apparatus as described above achieves a rapid pressure-change in the gas chamber 6. Because the apparatus is different from the conventional apparatus, the passage switch 16 thereof is not directly linked to the gas chamber 6, where the passage switch 16 is a solenoid valve and it acts as a resistance, utilized for discharging air. Further, in the case that the apparatus has such solenoid valve that directly links to the gas chamber 6 (as similar to the conventional apparatus), accident happens to the solenoid valve due to extraneous materials, such as dust, fluid and the like, from the connection coupling with the cutter 1. The apparatus of the present invention, however, such accident is difficult to happen, because the passage switch 16 is not contaminated with extraneous materials from the cutter 1.

Figure 2:
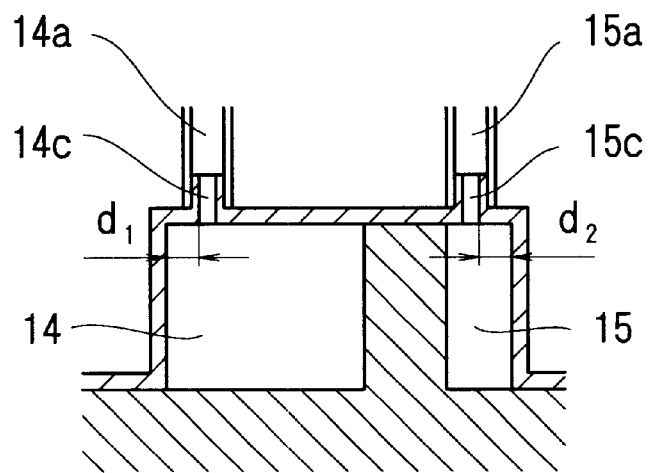
FIG. 2 is a view for illustrating a position of a draft hole provided for the second cylinder of the surgical apparatus for a vitreous shown in FIG. 1.

On a side wall of the second cylinder 12b, as shown in FIG. 2, there are provided the draft holes 14c and 15c, which are utilized for charging the separate chamber 14 and 15 with the compressed-air and for discharging the same. The draft hole 14c is positioned at a measure of d1 from a front end-face of the second cylinder 12b, and the draft hole 15c is positioned at a measure of d2 from a rear end-face (d1 and d2 may be found experimentally). Accordingly, the piston 13b which perform a reciprocating motion causes the separate chambers 14 and 15 to be closed space. In the closed space, by the effect produced by air, compressed by the piston 13b, the spaces can be used as a speed reduction section (to prevent the piston 13b from clashing into the front and back end-faces).

Figure 3:
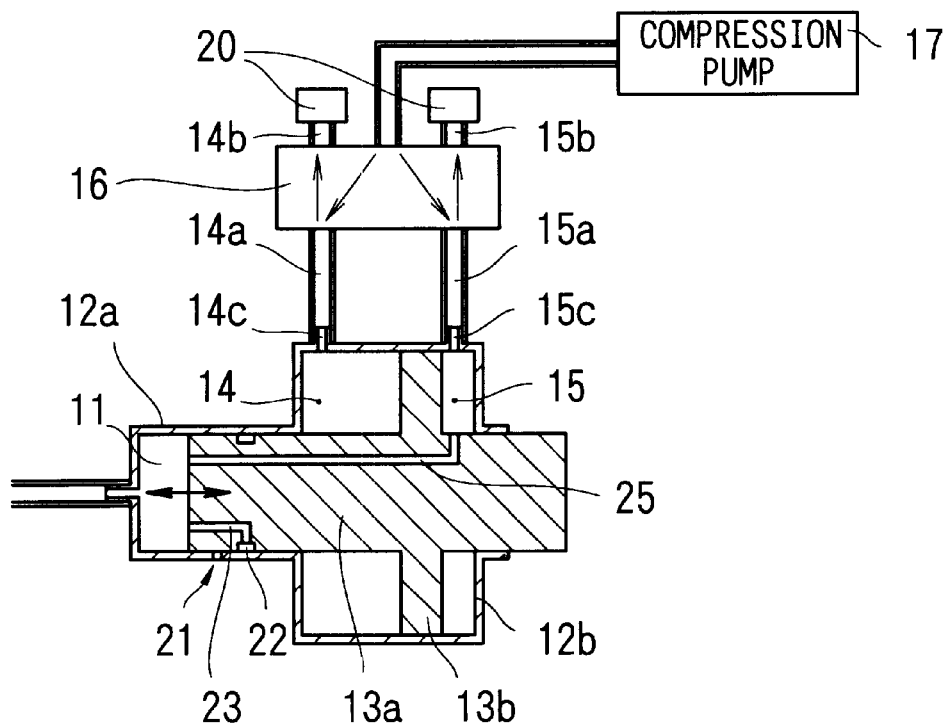
FIG. 3 is a view showing a schematic construction of an important part for describing an alternative embodiment of the apparatus.

Further, as shown in FIG. 3, by providing a small passage 25 which connects the gas chamber 11 with the separate chamber 15, the compressed-air of appropriate volume may circulate from the separate chamber 15 to the gas chamber 11. Accordingly, the air in the gas chamber 11 can be cooled down. Alternatively, a cooler may be provided instead.

Further, if a sectional area of the piston 13b, on which the compressed-air acts in the separate chamber 14 and 15, is made to be larger than that of the piston 13a, which compresses the gas chamber 11, then a pump 17, even if it is small, can exerts a strong force on the piston 13a. Thereby, the gas chamber 6 may be charged with sufficient compressed-air. Inversely, in the case of the apparatus which incorporates a compression bomb (gas cylinder) instead of the pump 17, a sectional area of the piston 13b is made to be smaller than that of the piston 13a, for the purpose of using a compressed-air of a high pressure, which is charged from the compression bomb. Accordingly, the small volume of a compressed-air can cause the inner tubular blade 4 to perform a reciprocating motion, thus achieving efficient use of a compression bomb. In this case, alternatively, another compressor for charging with a compressed-air of high-pressure may be prepared separately from a main body of the apparatus, so that the compressed-air can be conducted from the compressor.

Further, as a drive source used for causing the piston to reciprocate, an electric motor and an electromagnet may be used. In this case, not only the miniaturizing and lightening of the whole apparatus but also the convenience for handling are improved because the piston can be driven without using a compression pump and a compression bomb.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A surgical apparatus for removing a vitreous in an eyeball, comprising:

a cylinder;

a piston disposed in the cylinder so as to be capable of moving;

a moving device for reciprocating the piston in the cylinder; and a vitreous cutter comprising a first gas chamber which connects with a second gas chamber in the cylinder via a tube, an outer tubular blade having a hole, an inner tubular blade, a moving body which is capable of moving in a longitudinal axial direction of the outer tubular blade with holding the inner tubular blade, and an energisation device which causes the moving body to perform a backward movement toward the opposite side of the hole relative to the outer tubular blade;

wherein the inner tubular blade and the moving body being caused to perform a forward movement toward the hole relative to the outer tubular blade by a pressure rise in the first gas chamber, the pressure rise being caused by the forward movement of the piston, and to perform the backward movement relative to the outer tubular blade, which is accelerated by a negative pressure by a pressure fall in the second gas chamber connected to the first gas chamber via the tube, the pressure fall being caused by the backward movement of the piston.

2. The surgical apparatus according to claim 1, wherein the moving device comprising:

a supplying device for supplying compressed-gas which is utilized for causing the piston to perform the forward movement.

3. The surgical apparatus according to claim 2, wherein the supplying device comprising:

an exhaust hole which is utilized for exhausting gas from the cylinder.

4. The surgical apparatus according to claim 1, wherein the piston comprising:

a first piston; and a second piston being incorporated with the first piston in a body; and the cylinder comprising:

a first cylinder in which the first piston moves; and a second cylinder being incorporated with the first cylinder, in which the second piston moves.

5. The surgical apparatus according to claim 4, wherein the moving device comprising:

a supplying device which is utilized for supplying compressed-gas mutually to a third gas chamber and a fourth gas chamber in the second cylinder.

6. The surgical apparatus according to claim 5, wherein the supplying device comprising:

a first exhaust hole which connects with the third gas chamber; and a second exhaust hole which connects with the fourth gas chamber.

7. The surgical apparatus according to claim 5, further comprising:

a draft hole which allows the second gas chamber to be connected to the third gas chamber.

8. The surgical apparatus according to claim 1, further comprising:

devices for controlling a gas pressure by allowing the second gas chamber to be connected to outside air when the piston is at a given position in the cylinder, and by causing the second gas chamber not to be connected to the outside air when the piston is at a position except the given position.

* * * * *

UNITED STATES PATENT AND TRADEMARK OFFICE
CERTIFICATE OF CORRECTION

PATENT NO. : 6,383,203 B1
DATED : May 7, 2002
INVENTOR(S) : Kiyoshi Makihara

It is certified that error appears in the above-identified patent and that said Letters Patent is hereby corrected as shown below:

<u>Title page,</u>
ABSTRACT,
Line 6, delete "has" and insert -- gas --.

Signed and Sealed this

Sixth Day of August, 2002

Attest:

Attesting Officer

JAMES E. ROGAN
*Director of the United States Patent and Trademark Office*